United States Patent
Herrmann et al.

(10) Patent No.: US 9,233,797 B2
(45) Date of Patent: Jan. 12, 2016

(54) INSPECTION DEVICE FOR INSPECTING FOREIGN MATTER

(75) Inventors: Jürgen Herrmann, Rosenheim (DE); Wolfgang Schorn, Hönningen (DE)

(73) Assignee: KHS GmbH, Dortmund (DE)

( * ) Notice: Subject to any disclaimer, the term of this patent is extended or adjusted under 35 U.S.C. 154(b) by 247 days.

(21) Appl. No.: 13/991,957

(22) PCT Filed: Nov. 5, 2011

(86) PCT No.: PCT/EP2011/005576
§ 371 (c)(1),
(2), (4) Date: Jun. 6, 2013

(87) PCT Pub. No.: WO2012/076088
PCT Pub. Date: Jun. 14, 2012

(65) Prior Publication Data
US 2013/0248321 A1     Sep. 26, 2013

(30) Foreign Application Priority Data
Dec. 8, 2010   (DE) .................. 10 2010 053 771

(51) Int. Cl.
*G01N 29/04*      (2006.01)
*B65G 19/02*      (2006.01)
*G01N 29/22*      (2006.01)

(52) U.S. Cl.
CPC .............. *B65G 19/02* (2013.01); *G01N 29/046* (2013.01); *G01N 29/225* (2013.01); *G01N 2291/2695* (2013.01)

(58) Field of Classification Search
CPC ..... G01N 29/024; G01N 29/11; G01N 29/28; G01N 29/46; G01N 29/0672; G01N 29/2406; G01N 29/348; G01N 29/50; G01N 33/02; G01N 29/046; G01N 29/225
USPC .................. 73/596–600, 614–616, 624–630
See application file for complete search history.

(56) References Cited

U.S. PATENT DOCUMENTS 4,021,122 A * 5/1977 Krenmayr ................. 356/239.4
4,184,372 A   1/1980 Brown
(Continued)

FOREIGN PATENT DOCUMENTS

DE    202 17 559    1/2003
DE    202 18 138    4/2004
(Continued)

OTHER PUBLICATIONS

Delgado et al., FAU Erlangen-Nürnberg (AIF264ZBG), 1-4, 2009.

*Primary Examiner* — Helen Kwok
(74) *Attorney, Agent, or Firm* — Occhiuti & Rohlicek LLP

(57) ABSTRACT

An apparatus for transporting containers includes transport elements for transporting the containers in a transport direction, each of the transport elements including a clamping element, which is either a centering or holding element, for clamping a particular container, and an inspection device to inspect a container-to-be-inspected for unwanted foreign matter. The inspection device has a piezo sensor and is integral to the transport, centering, or holding element. The apparatus also includes an analysis unit connected to the inspection device, and an excitation element for controlling movement of a container. The inspection device is connectable to the container such that the container can be moved in an appropriate direction of movement and in the transport direction using the inspection device.

15 Claims, 4 Drawing Sheets

(56) References Cited

U.S. PATENT DOCUMENTS

| | | | |
|---|---|---|---|
| 4,208,915 A * | 6/1980 | Edwards | 73/620 |
| 4,651,568 A * | 3/1987 | Reich et al. | 73/612 |
| 4,821,573 A * | 4/1989 | Nagata et al. | 73/597 |
| 5,814,731 A * | 9/1998 | Alexander et al. | 73/644 |
| 5,861,548 A * | 1/1999 | Melvin et al. | 73/52 |
| 5,981,892 A * | 11/1999 | Baird et al. | 209/590 |
| 6,035,718 A * | 3/2000 | Lucas | 73/630 |
| 6,182,511 B1 * | 2/2001 | Lucas | 73/630 |
| 6,289,724 B1 | 9/2001 | Varma et al. | |
| 6,782,752 B2 * | 8/2004 | Basir et al. | 73/625 |
| 7,107,852 B2 * | 9/2006 | Hutchins et al. | 73/598 |
| 2013/0233437 A1 * | 9/2013 | Herrmann et al. | 141/1 |

FOREIGN PATENT DOCUMENTS

| | | |
|---|---|---|
| DE | 102 57 238 | 6/2004 |
| DE | 10 2004 051 961 | 5/2006 |
| DE | 10 2006 048 327 | 4/2008 |
| GB | 2 189 320 | 10/1987 |
| WO | WO03/029806 | 4/2003 |

* cited by examiner

INSPECTION DEVICE FOR INSPECTING FOREIGN MATTER

CROSS REFERENCE TO RELATED APPLICATION

This application is the national phase under 35 USC 371 of international application no. PCT/EP2011/005576, filed Nov. 5, 2011, which claims the benefit of the priority date of German application no. 10 2010 053 771.3, filed Dec. 8, 2010. The contents of the aforementioned applications are incorporated herein in their entirety.

FIELD OF DISCLOSURE

The invention relates to processing containers, and in particular, to detecting unwanted foreign matter in a container.

BACKGROUND

Bottles and similar containers are often used to hold liquids, such as drinks. The containers can be made of a transparent or translucent material, for example glass or a translucent plastic, e.g. PET.

It is known to use an inspection device to examine containers for unwanted foreign matter. This is done both to protect a consumer's health and a manufacturer's reputation.

Known methods and systems for foreign-matter inspection rely on optical inspection. However, optical methods do not work well in certain cases. For example, the containers to be inspected may be made of a dark glass or plastic. Or they may be opaque. Examples of opaque containers are metal cans. Optical systems also have difficulty when the product is very cloudy, or if it contains solids or fibers.

Also known is an inspection method in which, under laboratory conditions, a piezo sensor is used, such as the AiF short report on the 264 ZBG (new kind of multi-contact detection as the basis of an innovative hybrid system for the automatic detection of particulate solid foreign bodies in filled, flowable, non-lumpy food taking the example of products with a selected rheological constitution; Delgado, Antonio; Benning, Rainer; Forstner, Judith; Erlangen; FAU Erlangen-Nurnberg. 2009 (AIF264ZBG)).

The procedure disclosed in AIF264ZBG is reportedly suitable for recognizing foreign bodies in liquids by means of a signal detection by the piezo sensor and vibration analysis following excitation of the liquid. As containers, 0.5-liter bottles were used for the investigations conducted, as used for beer or alcohol-free drinks. For the numerical simulations by means of the finite elements method (ANSYS CFX simulation software), a bottle filled with water was selected by way of example, to investigate whether a translational or a rotational acceleration should prove to be more suitable. As foreign bodies, largely spherical glass particles measuring 0.5 mm, 1.0 mm and 1.5 mm in diameter were observed. In addition, initial theoretical investigations with PET particles but also with olive oil were carried out. Due to the adjustability of the top bottle centering and the flexible bearing of the base part, the clamping force can be set at a defined level. The latter also effects a comparatively simple implementation of the necessary uncoupling from vibrations acting from the outside. The signal pick-up or detection by the piezo sensor occurs here exclusively via the base of the bottle wherein the piezo sensor is in fact stuck directly onto the base of the bottle.

Fundamentally, thus, foreign matter could also be detected in containers and/or products that are optically difficult to inspect. However, the information in the short report is based solely on laboratory measurements.

SUMMARY

Among the objects of the invention is that of providing an improved container-handling installation that can more reliably detect unwanted foreign matter.

In one embodiment, the invention features a container-handling installation in which an inspection device includes a piezo sensor that is an integral component of a transport element, a centering element, and/or a holding element. The container-handling installation also has an excitation element that moves the container to be inspected in an appropriate direction of movement, halts this movement, and/or reverses this movement. The inspection device connects to the container such that the container moves with the inspection device in both the appropriate direction of movement and in a transport direction.

A container-handling installation according to the invention can, with its inspection device, reliably detect foreign matter inside the container, or within the product that is in a container. To do so, the container is clamped between the centering and holding elements. The excitation element then induces the container to move, and either abruptly halts or reverses this motion. As a result of its inertia, any foreign matter strikes the inner wall of the containers. In doing so, it makes a characteristic noise. The piezo sensor then detects this noise.

The container may also have solids that are desirable, and that would also make noise as they hit the container wall. In an effort to distinguish the two, the signal from the piezo sensor is fed to an analysis unit. The analysis unit determines whether the signal corresponds to unwanted foreign matter hitting the container wall or whether it corresponds to a desired solid. If the analysis unit determines that the signal is indicative of foreign matter, the corresponding container is removed at a subsequent station. Otherwise, it remains on the production line.

In some embodiments, the piezo sensor is an integral component of a structure that is either the transport element, the centering element, the holding element, or any combination thereof. As a result, the inspection device is disposed on the container-handling installation itself. The container to be inspected can thus be connected to the inspection device briefly, for the duration of the transport, such that it can be released if wanted. This can be done without having to firmly bond a piezo sensor to the container.

As used herein, a "centering element" includes a bell that holds the container upright.

In some embodiments, the inspection installation or the piezo sensor is an integral component of a bell of the container handling installation. In some of these embodiments, the piezo sensor is arranged on a bearing area of the bell. This bearing area is where the container bears against the bell. In other such embodiments, the piezo sensor is arranged in such a way that the bell is in contact with a seal on the container. Typical seals for cases in which the container is a bottle are a crown cork or a screw top. In a preferred embodiment, the piezo sensor is in contact with an external wall section of the container to be inspected.

In a further embodiment, the bell has a conical body, the top of which connects to a hollow cylindrical section. At the bottom, the conical body has a bearing element on which a piezo sensor is disposed. In some embodiments, the carrier element is an L-shaped structure having a main bar and a bottom bar connected to the main bar. In these embodiments, the carrier element is brought to rest, preferably by its main bar, on the outside of the container by spring action. The main bar can thus also be described as a spring bar. In a preferred embodiment, a number of carrier elements are disposed on the conical body, preferably evenly spaced around the circumference. In a further preferred embodiment, the piezo sensor is arranged in the main bar. This ensures a force-fitted and/or frictionally engaged contact of the piezo sensor with the container.

In some embodiments, a slip-ring assembly on the centering element or on the bell provides wired transmission of power and data to and from the piezo sensor. In other embodiments, the energy supply is an internal energy source that can be arranged on the centering element or on the bell.

In yet other embodiments, a transmitter provides wireless data transmission to a receiver.

In additional embodiments, the carrier element is made such that the particular piezo sensor can come to rest near an opening of the container to be inspected or in a top area of that container.

In other embodiments, the carrier elements have enough reach to cause a piezo sensor to rest on a belly area or between the bottom and the top of the container. Among these embodiments are those in which the carrier element has different reaches so that one piezo sensor can be brought to rest near the top of the container, while another piezo sensor can be brought to rest near the container's belly, near the container's bottom, or anywhere else on the container.

In some embodiments, the piezo sensor remains in contact with a container being inspected, regardless of which direction of movement and/or transport direction the latter carries out.

In some embodiments, the excitation element can induce the container to move not only around its vertical axis but also along it, or at an angle to it, and abruptly halt or even reverse this movement. This encourages any solids in the container, whether desired or otherwise, to hit the internal wall. The piezo sensor then measures the resulting vibration.

The bell and the plate together clamp the container so that it stands along its vertical axis. In a preferred embodiment, the excitation element is directly on a plate on which the container is held upright in the transport direction.

In some embodiments, the excitation element includes a rotary drive that induces the container to rotate around its vertical axis. Among these embodiments are those in which the excitation element is an autonomous drive, and those in which it is a rotary drive of known rotary plates.

In some embodiments, one or more piezo sensors are arranged on the plate. In others, one or more piezo sensors are integral components of the plate.

In another embodiment, carrier elements extend away from a standing space of the plate. In this embodiment, main bars of the carrier elements, which support piezo sensors, are in spring-like contact with an outer wall of the container. In some of these embodiments, those areas of the main bars that have the piezo sensors are in contact with the container. A similar embodiment uses the same principle but with the carrier elements instead extending from the bell. In both of these embodiments, there are examples in which carrier elements all have the same longitudinal reach and other examples in which the carrier elements all have different longitudinal reaches.

In yet embodiments, the carrier elements are arranged rigidly on the bell, on the carrier, or on other suitable locations. However, the carrier elements are movable so that they can move from a rest position into an inspection position and back. Movement can be caused in a variety of ways. In some of these embodiments, suitable drives are provided to move the carrier element along a vertical axis of a container to be examined. Examples of suitable drives include electromotive drives and pneumatic drives.

In some of these embodiments, the carrier element, with its measuring area, which is the area in which the piezo sensor is arranged, is movable from below. In these embodiments, the piezo sensor can be placed against the base of the container, or it can be moved past the base and placed on a belly area of the container. Similarly, in those embodiments that use a bell, the carrier element is movable from above so that the piezo sensor can be placed against the top of the container and moved down towards the belly of the container.

In some embodiments, the energy supply to drive the rotary drive, the carrier element, and/or for the piezo sensor is integrated into the plate. In other embodiments, it is external. Also among the embodiments are those that which a wired or wireless signal transmission from at least one piezo sensor to the analysis unit is possible.

In some embodiments, one or more piezo sensors are integrated into the plate itself. In some of these embodiments, the plate has at least one container carrier layer and one sensor layer. The plate thus has at least two layers. Among these embodiments are those in which the container carrier layer is arranged radially on an outer part of the plate and the sensor layer is inside the container carrier layer, so that it is centrally located on the plate.

Embodiments include those in which the material from which the carrier is made includes metal, glass, ceramic, gel, gel pads, liquids of a suitable kind, and technical fabric. In some embodiments, the carrier has a multi-layer structure.

In some embodiments, the piezo sensor or sensors are cast in the plate or in a metal baseplate. Among these embodiments are those in which the piezo sensor or sensors are in contact with the container surface. This enables them to more easily pick up the impact signal.

In some embodiments, the container-handling installation is a filling machine. In others, it is a labeling machine. In yet others, the container-handling installation is a sealer or an independent inspection installation that has other inspection tasks.

Additional embodiments include those that have a circumferential conveyance for conveying containers, and those that have a linear conveyance for conveying containers.

In those embodiments that have a circumferential conveyance, the inspection device can be arranged on an inlet star, a production star, a main star, or an outlet star. In some of these embodiments, a star provides an energy supply to the piezo sensor or sensors.

Among those embodiments that include a linear transporter are those that include an endlessly circulating transport element. An example of such a transport element is a conveyor belt. These embodiments include those in which a piezo sensor is arranged in the conveyor belt at a location that would correspond to a container's position on the belt. Thus, when a container is present on conveyor belt, the piezo sensor contacts the container. In other embodiments, the linear transporter has a bell and a plate. In these embodiments, the container is clamped between the bell and the plate.

In another aspect, the invention features a method for inspecting containers with an inspection device. Such a method includes holding the container as it moves along a transport direction, bringing a piezo sensor into contact with the container, the piezo sensor being an integral component of a transport element and/or a centering and/or holding element thereof, inducing the container to move, halting or reversing the induced movement, using the piezo sensor, picking up or detecting signals from particles impacting on the inner wall of the container, and forwarding or transmitting the signals thus picked up to an analysis unit that decides, based on the signals, whether or not the containers contains foreign matter.

In some practices of the method, individual steps are carried out a number of times. Among these are practices in which the individual steps are carried out repeatedly on a single container. Also among these practices are those that include repeatedly inducing the container to move, and halting or reversing the movement.

In those embodiments that have more than one piezo sensor, data sets from the individual piezo sensors are detected and analyzed concurrently.

Some practices include reversing the direction of movement directly without the intermediate halt stage, neglecting of course the extremely short interval that arises only because an instantaneous reversal of movement would technically require infinite force.

Some practices include causing a regular excitation, such as a pulsatile excitation.

Yet other practices include overlapping vertical and horizontal directions of movement, as well as vibrating a container to be inspected.

In some embodiments, the analysis unit comprises an amplifier, a computer, a converter and/or filter elements. Such an analysis unit can be part of a control unit.

Some embodiments also include amplifiers and/or filters on the data path from the piezo sensor to the analysis unit. These are used as part of the signal forwarding process.

In yet other embodiments, a signal picked up by the piezo sensor without a signal filter is passed on to the analysis unit. In these embodiments, all data processing and analysis takes place in the analysis unit.

BRIEF DESCRIPTION OF THE FIGURES

These and other features of the invention will be apparent from the following detailed description and the accompanying figures, in which.

In the various figures, the same parts are always given the same reference symbols, and hence they are generally also only described once.

DETAILED DESCRIPTION

Figure 1:
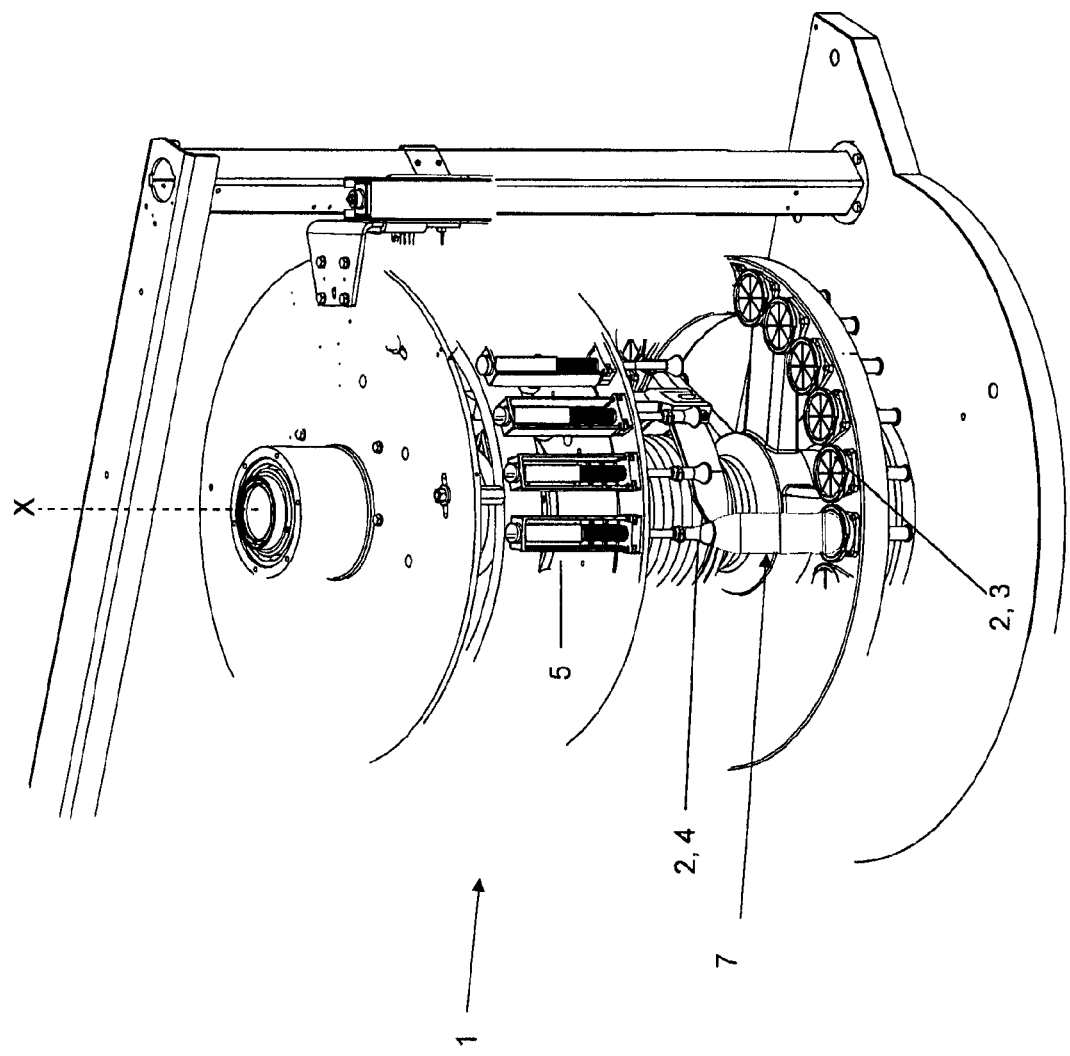
FIG. 1 shows a partial view of a container handling installation.

FIG. 1 shows a container-handling installation 1. In the particular embodiment shown, the container-handling installation 1 is a labeling machine or labeling carousel. The container-handling installation 1 has a number of transport elements 2. Each transport element 2 has a standing area 3 and a bell 4. The transport element 2 moves containers 7 along a transport direction. As used herein, the transport direction is the direction in which the container 7 travels to be supplied to individual consecutive processing stations and/or inspection stations.

In the particular embodiment shown, the standing area 3 is a rotary plate 3, and the bell 4 is mounted on a drive device 5 such that it can be raised and/or rotated. The rotary plate 3 and the bell 4 cooperate to rotate containers 7 around a central axis X of the container-handling device 1 and to feed them to processing units.

In operation, the base of a container 7 stands on a rotary plate 3. The bell 4 holds the container 7 at a top thereof and clamps the container between itself and the rotary plate 3. In the particular example, the containers 7 are PET bottles and the processing units are labeling units.

The container-treatment apparatus 1 includes a piezo sensor 8 that functions as an inspection device. The piezo sensor 8 is used in connection with inspecting the container for unwanted foreign matter. Preferably, the piezo sensor is an integral component of the bell 4, as show in FIG. 2, and/or the rotary plate 3, as shown in FIG. 3, i.e. as an integral component of the particular transport element 2.

Inspection devices other than a piezo sensor 8 can also be provided. These might be used, for example, to check the label position, or to orient the containers. These additional sensors are not, however, the subject of this invention.

The bell 4 and/or the rotary plate 3 induce the container 7 to move in a direction of movement. This direction of movement is a movement that is in addition to the movement in the transport direction. The direction of movement is generated independently of the movement in the transport direction. Thus, the direction of movement of the container 7 can be around the container's vertical axis, along that axis, at an angle to that axis, or any combination thereof.

A preferred direction of movement is a rotary movement of the container around its vertical axis. The rotary plate 3, with its rotary drive, is suitable for causing such movement because it can rotate at more than 1000 rpm. The rotary plate 3 is therefore not just a place for a container to stand. Nor is its role restricted to that of an orientation element. In fact, the rotary plate 3 has the additional function of an excitation element that induces the movement of the container 7. In some embodiments, however, it is the bell 4 rather than the rotary plate 3 that functions as the excitation element.

The inspection device 8, which in the illustrated embodiment is a piezo sensor 8, detects unwanted foreign matter. It does so even for products in which optical methods are unable to reliably detect foreign matter.

Figure 2:
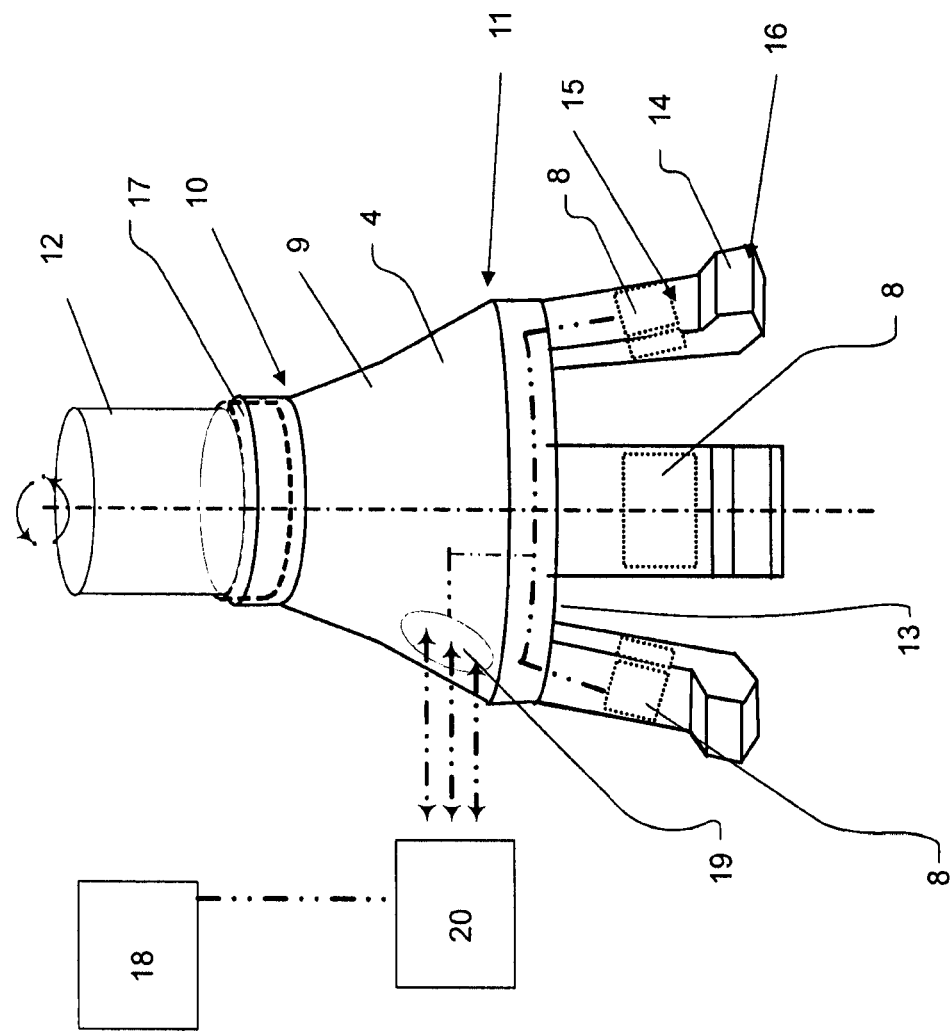
FIG. 2 shows a centering element.
Figure 3:
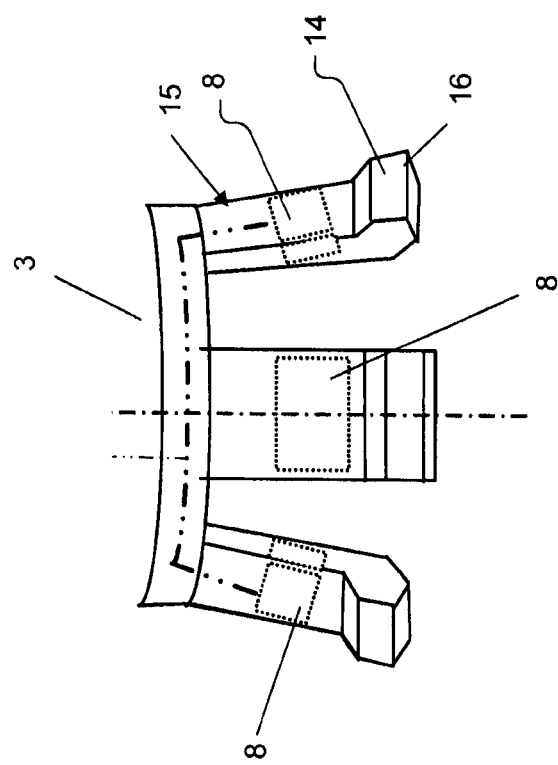
FIG. 3 shows a holding element.

In a first embodiment, shown in FIG. 2, the piezo sensor 8 is integrated into the bell 4. As a result, the bearing surface of the bell 4, which is where the bell 4 contacts a container 7, is a measuring area in which the piezo sensor 8 is arranged.

Referring now to the particular embodiment shown in FIG. 2, the bell 4 has a conical body 9, or cover, that extends from a top side 10 to a bottom side 11. A cylindrical section 12 is provided on the top side 10. This cylindrical section 12 can be connected to the drive device 5.

In contrast to known bells, the illustrated bell 4 has at least one carrier element 14 on a bottom face 13 thereof. As shown in FIG. 2, a number of carrier elements 14 are provided. These carrier elements 14 are distributed evenly spaced around the circumference of the bell 4.

Each carrier element 14 is L-shaped with a main bar 15 and a base bar 16. The base bar 16 is oriented radially outwards from the main bar 15. The main bar 15 is a spring bar. When a container is in place, the main bar 15 lies on an outer side of the container 7 and exerts a spring force against an opening section or side-wall section of the container 7.

Preferably, at least one piezo sensor 8 is integrated into each main bar 15. The piezo sensors 8 are integrated, in such a way that, when the bell 4 engages a container 7, the piezo sensor 8 contacts an external surface of the container 7. As can be seen in FIG. 2, all piezo sensors 8 come into contact with the surface of the container 7.

The piezo sensor 8 requires energy to operate. In the illustrated embodiment, this energy comes from a slip-ring transmitter 17 that is on the top of the conical body 9. The slip-ring transmitter 17 can also be used as the data transmitter to communicate data from the piezo sensor 8 to an analysis unit 18. Dashed lines for carrying energy and data are shown in FIG. 2.

In some embodiments, each bell 4 has its own internal energy supply and a wireless data transmitter 19 that communicates with a receiver 20 that connects to the analysis unit 18.

Figure 4:
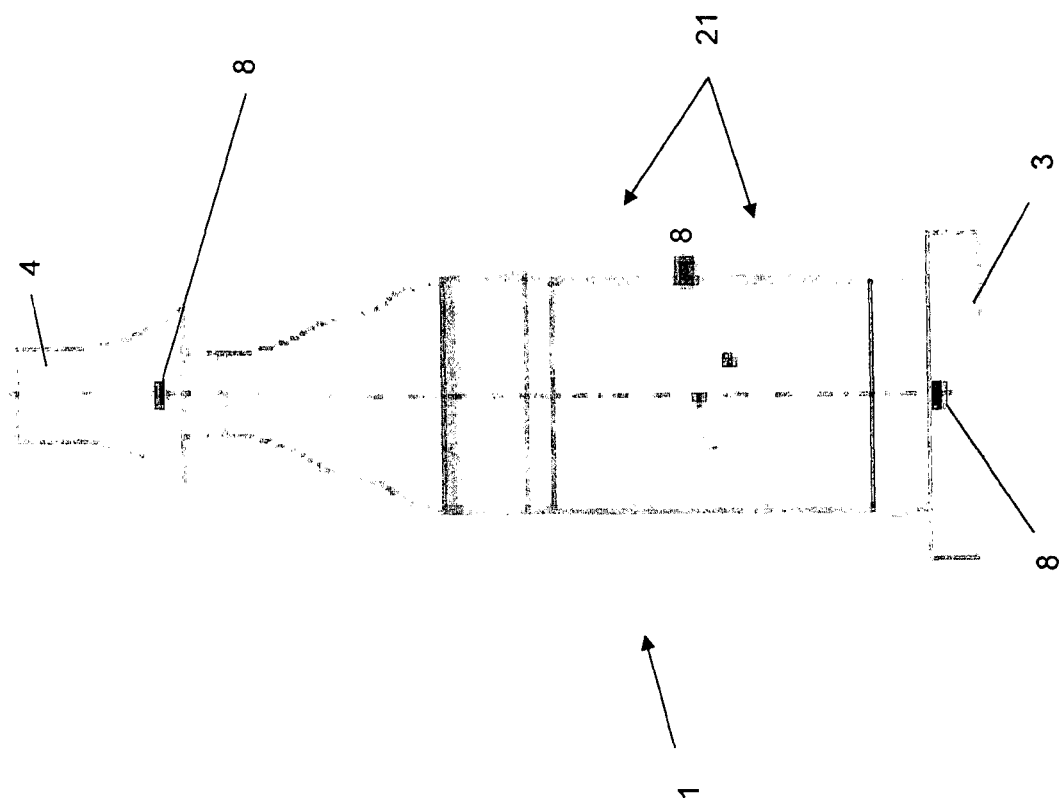
FIG. 4 shows measuring areas on a container.

In the embodiment shown in FIG. 2, all carrier elements 14 have the same longitudinal reach. It is also possible to make the various carrier elements 14 with different longitudinal reaches so that they extend down along the container by different distances. In particular, FIG. 4 shows a first piezo sensor 8 in contact with a belly area 21 of the container 7 and a second piezo sensor 8 arranged in the container's opening area 22. As shown in FIG. 4, there may be several piezo sensors 8 located at various places on the container.

It is also feasible for each carrier element 14 to be made so that it can be moved in its longitudinal direction individually so that a piezo sensor 8 can be placed almost anywhere one the container 7 by moving the piezo sensor 8 along the longitudinal axis of the carrier element 14. To do so, the carrier elements 14 can be moved from a rest position into a freely selectable measuring or inspection position.

Like the bell 4, the rotary plate 3 can have carrier elements 14 that encompass lateral portions of the container's base area. Each carrier element 14 has at least one piezo sensor 8 integrated into it.

FIG. 3 shows an embodiment in which a standing area of the rotary plate 3 on which the container stands is oriented towards the bottom edge of the drawing. The carrier elements 14 of the plate 3 are oriented towards the bell 4. The external energy supply to the carrier elements 14, and in particular, to the piezo sensors 8, can be a slip ring, an inductive conveyor, and/or a dynamo supply as was discussed in connection with the bell 4. Moreover, a data connection to the analysis unit 18 can be provided as discussed in connection with the bell 4.

In some embodiments, the carrier element 14 is movable on the rotary plate 3.

In other embodiments, a movable carrier element 14 is disposed centrally in the rotary plate 3. The movable carrier element 14 measure the outer surface of the base of the container.

Yet other embodiments include a moveable carrier element 14 integrated in the bell 4 so as to lie on the seal in order to be able to carry out the measurement.

Other embodiments in include those that integrate the piezo sensor 8 in a rotary plate 3 made with multiple layers. In some of these embodiments, one layer is a carrier layer that carries the container 7, and another layer is a sensor layer. The carrier layer is arranged radially on an outer part, whereas the sensor layer is arranged centrally.

In other embodiments, the bell 4 is on the bearing area for the container 7 and has a carrier layer and a sensor layer.

The excitation element sets the container 7 in rotation. This rotation, in turn, carries along any liquid in the container. Solids in the liquid, whether the solids are foreign matter or a desired constituent part of the contents, eventually impact the inner wall of the container 7. One or more piezo sensors 8 record the energy transfer associated with this impact and provide the data to the analysis unit 18. The analysis unit 18 carries out signal processing to determine whether the recorded impact came from a foreign body or from desired solids, if any.

The piezo sensor 8 can be arranged not only on the labelling machine but also on filling machines, sealing machines, and any similar container-handling installations. These container-handling installations can be made rotary conveyors or linear conveyor. In the case of a linear conveyor, at least one piezo sensor 8 can be integrated into a linear conveyor belt. Alternatively, the piezo sensor 8 can be integrated in the drive axle of a conveyor belt so that it rotates with this drive axle.

In those embodiments in which the container-handling installation is a sealing machine, the inspection device 8 is a piezo sensor that is an integral component of the sealing head. The piezo sensor 8 in this case does not have to just contact with the outer wall of the container. It can also contact a sealing element, such as a crown cork, or a screw cap. In addition, when many piezo sensors are present, at least one piezo sensor is oriented parallel to the sealed opening.

In the foregoing embodiment, inspection for unwanted foreign matter can take place at the same time as container is sealed. In other embodiments, sealing is carried out first, followed by inspection.

The piezo sensors can also be used for other functions. For example, it is possible to use the piezo sensor to carry out a cap-sit check and/or a leak test on the seal.

In some embodiments, piezo sensors as described herein determine a quantity of product in the container by weighing it.

In yet other embodiments, piezo sensors are integrated in grab sections and/or in plates of filling machines.

Additional embodiments include those in which the piezo sensor measures without contact.

The invention claimed is:

1. An apparatus for transporting containers, said apparatus comprising a container handling installation, said container handling installation comprising transport elements for transporting said containers in a transport direction, each of said transport elements comprising a clamping element for clamping a particular container, said clamping element being selected from the group consisting of a centering element and a holding element, an inspection device to inspect a container-to-be-inspected for unwanted foreign matter, said inspection device comprising a piezo sensor and being an integral component of a structure selected from the group consisting of said transport element, said centering element, and said holding element, an analysis unit connected to said inspection device, an excitation element configured for controlling movement of a container-to-be-inspected, wherein controlling movement of said container-to-be-inspected comprises carrying out a movement selected from the group consisting of moving said container-to-be-inspected in a particular direction, reversing movement of said container-to-be-inspected, and halting movement of said container-to-be-inspected, whereby said inspection device is connectable to said container-to-be-inspected such that said container-to-be-inspected can be moved in an appropriate direction of movement and in said transport direction using said inspection device.

2. The apparatus of claim 1, wherein said inspection device is an integral component of an element selected from the group consisting of said centering element and said holding element of said container handling installation.

3. The apparatus of claim 1, wherein said inspection device is connected to a side wall area of said container.

4. The apparatus of claim 1, wherein at least one of said centering element and said holding element comprises a carrier element, said carrier element comprising said inspection device as an integral component thereof.

5. The apparatus of claim 1, further comprising carrier elements that can be moved from a rest position into a measuring position, wherein said inspection device is integrated into one of said carrier elements.

6. The apparatus of claim 1, wherein said excitation element is configured to induce said container-to-be-inspected to move around a vertical axis thereof.

7. The apparatus of claim 1, wherein said excitation element is configured to induce said container-to-be-inspected to move along a vertical axis thereof.

8. The apparatus of claim 1, wherein said excitation element is configured to induce said container-to-be-inspected to move so as to form an angle relative to a vertical axis thereof.

9. The apparatus of claim 1, wherein said centering element comprises a bell, and wherein said holding element comprises a plate.

10. The apparatus of claim 1, wherein said holding element comprises a sensor layer and a carrier layer.

11. A method for internal inspection of containers in a container handling installation as recited in claim 1, said method comprising holding a container in said transport direction, bringing said piezo sensor into contact with said container, inducing said container to move, at least one of halting and reversing said induced movement, using said piezo sensor, picking up signals from particles impacting on an inner wall of said container, and forwarding a signal to an analysis unit that determines whether or not said container contains foreign matter, wherein said signal is selected from the group consisting of signals picked up and electrical data signals derived from said signals picked up.

12. The method of claim 11, wherein forwarding said signal comprises amplifying and filtering said signal.

13. The method of claim 11, further comprising amplifying said signal when forwarding said signal, and, at said analysis unit, filtering said signal.

14. The method of claim 11, wherein inducing movement of said container comprises repeatedly inducing said movement.

15. The method of claim 11, further comprising receiving data from a number of inspection devices simultaneously, and analyzing said data simultaneously.

* * * * *